United States Patent [19]

Butler et al.

[11] Patent Number: 4,621,097

[45] Date of Patent: Nov. 4, 1986

[54] SATURATED CYCLOALKYL[c] PYRROLE-2(1H)-ACETIC ACID AMIDES AND DERIVATIVES THEREOF

[75] Inventors: Donald E. Butler; John G. Topliss, both of Ann Arbor, Mich.

[73] Assignee: Warner-Lambert Company, Morris Plains, N.J.

[21] Appl. No.: 766,387

[22] Filed: Aug. 16, 1985

[51] Int. Cl.[4] .................. A61K 31/40; C07D 209/46; C07D 209/52
[52] U.S. Cl. .................................... 514/421; 514/212; 514/323; 514/414; 546/200; 548/465; 548/512; 540/602
[58] Field of Search ................ 548/465, 512; 546/200; 260/245.7; 514/421, 414, 323, 212

[56] References Cited

U.S. PATENT DOCUMENTS

| | | | |
|---|---|---|---|
| 3,947,451 | 3/1976 | Jonsson et al. | 548/465 |
| 3,972,994 | 8/1976 | Beregi et al. | 548/512 |
| 4,145,347 | 3/1979 | L'Italien et al. | 546/208 |
| 4,350,691 | 9/1982 | Hadley et al. | 260/245.7 |

OTHER PUBLICATIONS

Chim. Ber., 98, 1928–37 (1965).

*Primary Examiner*—Donald G. Daus
*Assistant Examiner*—Mary E. Ceperley
*Attorney, Agent, or Firm*—Elizabeth M. Anderson

[57] ABSTRACT

A unique series of saturated cycloalkyl[c]-pyrrol-2(1H)-acetic acid amides are useful as agents for the reversal of amnesia. Intermediates for preparing the compounds, pharmaceutical composition containing the compounds, and methods for using the pharmaceutical compositions for treating senility and for the reversal of amnesia are described.

21 Claims, No Drawings

SATURATED CYCLOALKYL[c] PYRROLE-2(1H)-ACETIC ACID AMIDES AND DERIVATIVES THEREOF

BACKGROUND OF THE INVENTION

A synthesis of 2-aminomethyl-cyclohexan-carboxylic acid-(1) lactam is described in Chem. Ber., 98, 1928–37 (1965).

SUMMARY OF THE INVENTION

One aspect of the present invention is a generic compound having the structural formula

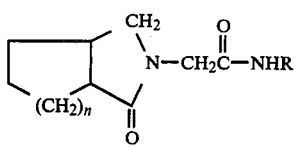

VI wherein n is one, two, or three and R is H or (CH$_2$)n'N(R'R''), wherein n' is two or three, R' and R'' are each independently hydrogen or a straight or branched alkyl of from one to six carbon atoms or when taken with the nitrogen atom form a five to seven membered ring which may be substituted by one or more alkyl groups of from one to four carbon atoms, or pharmaceutically acceptable acid addition salts of the compound containing a basic amine.

Another aspect of the present invention is a method of preparing a compound of Formula VI which comprises (a) reacting an alpha-carboalkoxy cycloalkanone with HCN to form the corresponding carboalkoxycycloalkanone cyanohydrin, (b) reacting the carboalkoxycycloalkanone cyanohydrin with POCl$_3$ in pyridine to form a 2-cyanocycloalkenylcarboxylic acid ethyl ester, (c) hydrogenating the 2-cyanocycloalkylcarboxylic acid alkyl ester to form hydro-1-oxo-2(1H)-cycloalkyl[c]pyrrole, (d) reacting the pyrrole with NaH and an alpha-bromoacetate to form the corresponding pyrrole acetic acid alkyl ester, and (e) reacting the ester with ammonia or a primary amine to form the corresponding amide.

A third aspect of the present invention is a pharmaceutical composition which comprises an effective amount of a compound of structural Formula I above in combination with a pharmaceutically acceptable carrier.

A fourth aspect of the present invention is a method of treating senility in a mammal comprising administering to a mammal an effective amount of the above identified pharmaceutical composition.

A fifth aspect of the present invention is a method of reversing amnesia in a mammal comprising administering to the mammal an effective amount of the above identified pharmaceutical composition.

DETAILED DESCRIPTION

Compounds of the formula

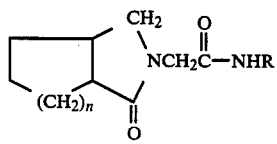

VI may be prepared from the corresponding cycloalkanones by the following schematic procedure:

SYNTHETIC SCHEME

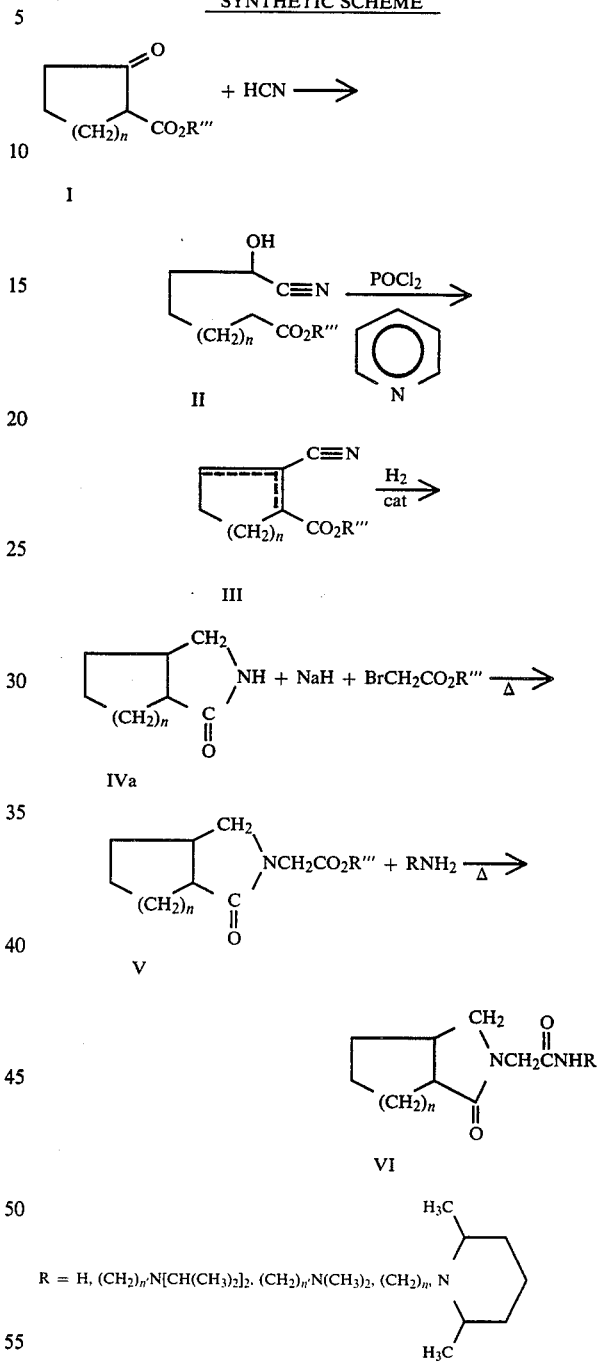

R = H, (CH$_2$)n'N[CH(CH$_3$)$_2$]$_2$, (CH$_2$)n'N(CH$_3$)$_2$, (CH$_2$)n', N n = 1,2,3
n' = 2,3

For example, the preparation of representative preferred embodiment of the cis and trans isomers of the compounds is as follows.

2-Carboalkoxy-cycloalkanone is treated with hydrogen cyanide to give the derived cyanohydrin. This compound is treated with phosphorus oxychloride to produce the corresponding cyanocycloalkenylcarboxylic acid alkyl ester.

For example, a solution of hydrogen cyanide (100 ml) in ethanol (80 ml) containing saturated aqueous potassium cyanide (2 ml) is treated over 20 minutes with a solution of 2-carboethoxycycloheptanone (44.2 g, 0.24 mole) in ethanol (50 ml) at 0° C. The mixture is stirred 24 hours at 25° C. and carefully treated with a saturated aqueous solution of oxalic acid (9 ml). The mixture is filtered and concentrated at reduced pressure. The oil is taken up in diethyl ether and dried (MgSO$_4$). The suspension is filtered and concentrated at reduced pressure to yield 2-carboethoxy-cycloheptanone cyanohydrin (II) as an oil. A solution of 2-carboethoxy-cycloheptanone cyanohydrin (24.5 g, 0.11 mol) in pyridine (82 ml) and toluene (82 ml) is added to a preformed ice-cold solution of phosphorous oxychloride (68.5 g, 0.42 mole) in pyridine (98 ml) at 0° C. The solution is maintained at 0° C. for 24 hours and then slowly warmed to 80° C. and maintained at 80° C. for five minutes. The solution is poured onto ice (800 g) and the organic layer is separated. The aqueous layer is extracted with toluene (4×500 ml). The combined extracts are dried (MgSO$_4$), filtered, concentrated, and distilled to yield a mixture of 2-cyano-cycloheptenecarboxylic acid ethyl ester (III), and 7-carboethoxy-cycloheptenecarbonitrile (III) with a bp 85°–86° C. at 1 mm.

A cyanocycloalkenyl-carboxylic acid ester is hydrogenated under pressure in the presence of a catalyst to form the corresponding cycloalkyl[c]pyrrole.

For example, a solution of a mixture of 2-cyano-cycloheptene-carboxylic acid ethyl ester and 7-carboethoxycycloheptenecarbonitrile in tetrahydrofuran (150 ml) and triethyl amine (5 ml) is treated with hydrogen gas in the presence of Raney-Cobalt (5 g) at 8000 psig. After hydrogen uptake stops, the suspension is filtered and concentrated to yield a crystalline solid with mp 145°–146° C. This is a mixture of octahydro-1-oxo-2(1H)-cyclohepta[c]pyrrole IV and hexahydro-1-oxo-2(1H)-cyclohepta[c]pyrrole IV(a) with the unsaturation between the two rings.

A cycloalkyl[c]pyrrole is treated with sodium hydride and an alkyl alpha-bromoacetate to form a cycloalky[c]pyrrole acetic acid alkyl ester.

For example, a solution of octahydro-1-oxo-2(1H)-cyclohepta[c]pyrrole (12.7 g, 0.08 mole) in a mixture of 50:50 toluene-tetranydrofuran (250 ml) is heated to reflux and 60% sodium hydride in mineral oil (3.5 g, 0.085 mole) is added, after refluxing one hour the mixture is cooled and ethyl alpha-bromoacetate (14.2 g, 0.085 mole) is added dropwise. The tetrahydrofuran is allowed to distill out until the reaction mixture reaches 110° C. The mixture is heated at reflux 1.5 hours, cooled, and diluted with wet diethyl ether. The mixture is filtered through filter aid, concentrated at reduced pressure, and washed with n-pentane. The oil is distilled to yield cis-octahydro-1-oxo-cyclohepta[c]pyrrole-2-(1H)-acetic acid ethyl ester (V) with a boiling point of 115°–117° C. at 0.1 mm pressure.

Another example of a preparation of the compounds represented by Formula V is illustrated by the following.

A solution of cis-hexahydro-1-oxo-2(1H)cyclopenta[c]pyrrole (IV) (10.5 g, 0.084 mole) in tetrahydrofuran (150 ml) is treated with 50% sodium hydride (7.2 g, 0.15 mole) that was washed with toluene (three times 100 ml). The mixture is stirred one hour at room temperature and ethyl bromoacetate (33.4 g, 0.2 mole) is added. The mixture is heated at 60° C. for 20 hours, cooled, and sodium hydride (0.5 g, 0.01 mole) is added, followed by ethyl alphabromoacetate (7.25 g, 0.045 mole). The mixture is stirred and heated at 60° C. for one hour. The mixture is cooled and filtered. The filtrate is concentrated at reduced pressure and distilled to yield cis-hexahydro-1-oxo-cyclopenta[c]pyrrole2(1H)-acetic acid ethyl ester (V), bp 99°–103° C. at 0.13 mm, that is slightly crude and is used as such.

A third example for the preparation of a compound represented by Formula V is as follows.

A solution of cis-octahydro-1-oxo-2H-isoindole (IV) or trans-octahydro-1-oxo-2H-isoindole (IV) (69.6 g, 0.5 mole) in tetrahydrofuran (400 ml) is treated with 55% sodium hydride (24.0 g, 0.55 mole) in mineral oil. The mixture is stirred one hour and ethyl alpha-bromoacetate (83.5 g, 0.5 mole) is added and the mixture is stirred at room temperature for one hour and heated at reflux for one hour. The mixture is cooled and 55% sodium hydride (1.2 g, 0.05 mole) is added, followed by ethyl alpha-bromoacetate (8.25 g, 0.05 mole). The mixture is refluxed one hour, cooled, and treated with water (10 ml). The solution is filtered and concentrated at reduced pressure. The resulting oil is washed with pentane to remove mineral oil and the oil is distilled to yield a mixture of the corresponding cis or trans-octahydro-1-oxo-2H-isoindole-2-acetic acid ethyl ester (V), mp 90°–92° C. at 0.075 mm.

A cycloalkyl[c]pyrrole acetic acid alkyl ester is treated with ammonia or an amine in methanol at room temperature or heated to yield the corresponding acetic acid amide.

For example, trans-octahydro-1-oxo-cyclohexa[c]pyrrole-2(1H)acetic acid ethyl ester (V) (6.6 g, 0.031 mole) in methanol is saturated with anhydrous ammonia and the mixture is stirred at room temperature 24 hours. The solution is concentrated at reduced pressure to yield a solid. Recrystallization from acetonitrile yields pure trans-octahydro-1-oxo-2H-isoindole-2-acetic acid amide (VI).

The preferred compounds are those of Formula VI wherein R is H, $(CH_2)_n$'N(R'R'') in which n' is two or three, R' and R'' are each independently hydrogen or a straight or branched alkyl of from one to six carbon atoms or combined with the nitrogen to form 1-pyrrolidinyl or 1-piperidinyl, optionally substituted with one or more lower alkyl groups, and n is one, two, or three.

Particularly valuable compounds falling within the scope of the present invention include the following compounds and their stereoisomers: cis-octahydro-1-oxo-2H-isoindole-2-acetic acid amide; trans-octahydro-1-oxo-2H-isoindole-2-acetic acid amide; cis-octahydro-1-oxo-2H-isoindole-2-acetic acid amide, N-[[2-bis(1-methylethyl)amino]ethyl].hydrochloride; cis-hexahydro-1-oxo-cyclopenta[c]pyrrole-2(1H)-acetamide; and cis-octahydro-1-oxo-cyclohepta[c]pyrrole-2(1H)-acetamide.

The compounds of the present invention are useful for treating senility or for reversing amnesia.

The effectiveness of the aforementioned compounds is determined by a test designed to show a compound's ability to reverse amnesia produced by electroconvulsive shock. The test is fully described in U.S. Pat. No. 4,145,347, issued Mar. 20, 1979, and is herein incorporated by reference. The only differences being that the test compounds in the present instance are administered orally and the length of the electroconvulsive shock is 1.0 seconds in duration.

The following criteria are used in interpreting the amnesia reversal percentage scores: 40 percent or more (Active=A), 25 to 39 percent (Borderline=C), and 0 to 24 percent (Inactive=N).

Table 1 below reports the percent of amnesia reversal of orally administered: cis-octahydro-1-oxo-2H-isoindole-2-acetic acid amide; cis-octahydro-1-oxo-2H-isoindole-2-acetic acid amide N-[2-[bis[1-methylethyl]amino]ethyl].hydrochloride; cis-octahydro-1-oxocyclohepta[c]pyrrole-2(1H)-acetamide; cis-hexahydro-1-oxo-cyclopenta[c]pyrrole-2(1H)-acetamide.

TABLE 1

| Structure | mg/kg | | |
|---|---|---|---|
| | 80 | 20 | 5 |
| (cis-octahydroisoindole)NCH$_2$CNH$_2$ | 64(A) | 85(A) | 78(A) |
| | *69(A) | 85(A) | 54(A) |
| (cis-octahydroisoindole)NCH$_2$CNH(CH$_2$)$_2$N[CH(CH$_3$)$_2$]$_2$ | 70(A) | 30(C) | 10(N) |
| | 100 | 10 | 1 |
| (cycloheptapyrrole)NCH$_2$CNH$_2$ | 31(C) | 58(A) | 46(A) |
| (cyclopentapyrrole)N—CH$_2$CNH$_2$ | 30(C) | 20(N) | 20(N) |

*Replication test

The compounds of the present invention include solvates and hydrates and pharmaceutically acceptable salts of the basic compounds of the present invention.

The term pharmaceutically acceptable salt is intended to mean a relatively nontoxic acid addition salt, either from inorganic or organic acids.

The alkyl groups of the present invention comprise both straight and branched carbon chains of from one to about six carbon atoms. Representatives of such groups are methyl, ethyl, isopropyl, 3-methyl, pentyl, and the like.

In addition, the stereochemistry of the ring junctures between the fused rings may be either cis or trans. This latter possibility for geometrical isomerism is limited to some extent by the difficulty of forming trans-ring junctures in fused-ring systems involving five-membered lactam rings. For example, it is apparently not possible to synthesize structures in which a five-membered lactam ring is joined in a trans-configuration to another five-membered ring.

Further, for those compounds of the present invention in which the molecule has no plane of symmetry, steroisomerism is possible.

The present invention contemplates all possible ring-size variants, geometric isomers, and stereoisomers of the compounds depicted generically by structural Formula VI given above.

The terms "stereoisomers," "stereoisomerism," "optical isomerism, " "optical isomers," "geometrical isomerism," and "geometrical isomers" as used through-out this specification and appended claims are those commonly employed by practitioners of the organic chemical art, specifically as defined on pages 1-6 of Eliel, "Stereochemistry of Carbon Compounds," McGraw-Hill, New York, 1962, incorporated herein by reference.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the fomulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogenously therein by stirring. The molten homogeneous mixture is then poured into convenient sized molds, allowed to cool, and thereby solidify.

Liquid form preparations include solutions, suspensions, and emulsions. As an example may be mentioned water or water propylene glycol solutions for parenteral injection. Liquid preparations can also be formulated in solution in aqueous polyethyleneglycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such as used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatable therapeutic agents.

In therapeutic use as cognition activators, the mammalian dosage range for a 70 kg subject is from 1 to 1500 mg of body weight per day or preferably 25 to 750 mg of body weight per day optionally in divided portions. The dosages, however, may be varied depending upon the requirements of the patient, the severity of the condition being treated, and the compound being employed. Determination of tne proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

Preparation of cis-octahydro-1-oxo-2H-isoindole-2-acetic acid amide

A solution of cis-octahydro-1-oxo-2H-isoindole-2acetic acid ethyl ester (17.79 g, 0.079 mole) in methanol (100 ml) is saturated with anhydrous ammonia and the solution is stirred 18 hours at room temperature. The solution is concentrated at reduced pressure to yield a gummy solid. Recrystallization from acetonitrile yields pure cis-octahydro-1-oxo-2H-isoindole-2-acetic acid amide, with mp 142°–144° C.

EXAMPLE 2

Preparation of cis-octahydro-1-oxo-2H-isoindole-2-acetic acid amide N-[2-[bis[1-methylethyl]amino]ethyl]hydrochloride A solution of cis-octahydro-1-oxo-2H-isoindole-2-acetic acid ethyl ester (11.26 g, 0.05 mole) and N-2-[bis[1-methylethyl]amino]ethylamine (10.10 g, (0.0725 mole) is heated at 100° C. for 24 hours. The solution is concentrated at reduced pressure and chromatographed over silica gel (elution with dichloromethane:methanol; 92.5:7.5). The eluate is concentrated at reduced pressure and the residue is treated with a saturated solution of hydrogen chloride in 2-propanol. The solution is diluted with anhydrous diethyl ether and allowed to stand for 24 hours at room temperature while precipitation of the hydrochloride slowly occurs.

Recrystallization from acetonitrile yields pure cis-octahydro-1-oxo-2H-isoindole-2-acetic acid amide N-2[bis[1-methylethyl]amino]ethyl.hydrochloride with mp 147°–148° C.

EXAMPLE 3

Preparation of cis-octahydro-1-oxo-cyclohepta[c]pyrrole-2(1H)-acetamide

A solution of cis-octahycro-1-oxo-cyclohepta[c]pyrrole-2-(1H)-acetic acid ethyl ester (3.7 g, 0.0154 mole) in methanol (75 ml) is saturated with anhydrous ammonia and stirred at room temperature 72 hours. The solution is concentrated at reduced pressure to yield a crystalline solid with mp 145°–147° C. Recrystallization from tetrahydrofuran yields pure cis-octahydro-1-oxo-cyclohepta[c]pyrrole-2-(1H)acetamide with mp 150°–151° C.

EXAMPLE 4

Preparation of cis-hexahydro-1-oxo-cyclopenta[c]pyrrole-2(1H)-acetamide

A solution of cis-hexahydro-1-oxo-cyclopenta[c]pyrrole-2(1H)-acetic acid ethyl ester (25 g, 0.0154 mole) in methanol is saturated with anhydrous ammonia and the mixture is stirred at room temperature 24 hours. The solution is concentrated at reduced pressure to yield a solid with mp 138°–141° C. Recrystallization (acetonitrile) yields pure cis-hexahydro-1-oxo-cyclopenta[c]pyrrole-2(1H)-acetamide with mp 142.5°–143.5° C.

We claim:

1. A compound having the structural formula

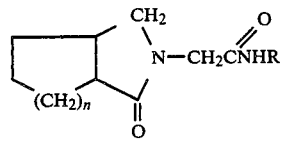

wherein n is one, two, or three; R is H, $(CH_2)_{n'}N(R'R'')$, in which n' is two or three; R' and R" are each independently hydrogen or a straight or branched alkyl of from one to six carbon atoms or combined with the nitrogen to which they are attached form a five to seven-membered ring which may optionally be substituted with one or more alkyl groups of from one to four carbon atoms or pharmaceutically acceptable acid addition salts of the compound when R is $(CH_2)_{n'}N(R'R'')$.

2. A compound according to claim 1 wherein R' and R" are each independently hydrogen or a straight or branched alkyl of from one to six carbon atoms or combined with the nitrogen to which they are attached equal 1-pyrroidinyl or 1-piperidinyl optionaly substituted with one or groups of alky of from one to four carbon atoms, or pharmaceutically acceptable acid addition salts of the compound when R is $(CH_2)_{n'}N(R'R'')$.

3. A compound according to claim 1 wherein n is one.

4. A compound according to claim 1 wherein n is two.

5. A compound according to claim 1 wherein n is three.

6. A compound according to claim 1 wherein R is H.

7. A compound according to claim 2 wherein R is $(CH_2)_n{}'N(R'R'')$.

8. A compound according to claim 7 wherein R' and R" are $CH_3$.

9. A compound according to claim 7 wherein R' and R" are $C_2H_5$.

10. A compound according to claim 7 wherein R' and R" are $CH(CH_3)_2$.

11. A compound according to claim 7 wherein R' and R" (when taken together with nitrogen are $-(CH_3)CH(CH_2)_3CH(CH_3)-$.

12. A compound according to claim 7 wherein n' is two.

13. A compound according to claim 7 wherein n' is three.

14. A compound according to claim 1 having the name cis-octahydro-1-oxo-2H-isoindole-2-acetic acid amide.

15. A compound according to claim 1 having the name trans-octahydro-1-oxo-2H-isoindole-2-acetic acid amide.

16. A compound according to claim 1 having the name cis-octahydro-1-oxo-2H-isoindole-2-acetic acid amide, N-[2-[bis[-1-methylethyl)amino)]ethyl].hydrochloride.

17. A compound according to claim 1 having the name cis-hexahydro-1-oxo-cylopenta[c]pyrrole-2(1H)-acetamide.

18. A compound according to claim 1 having the name cis-octahydro-1-oxo-cyclohepta[c]pyrrole-2(1H)-acetamide.

19. A cognition activating pharmaceutical composition comprising an effective amount of a compound as defined in claim 1 in combination with a pharmaceutically acceptable carrier.

20. A method of treating senility in mammals comprising administering to said mammal an effective amount of a pharmaceutical composition in accordance with claim 19.

21. A method of reversing amnesia in mammals comprising administering to said mammal an effective amount of a pharmaceutical composition in accordance with claim 19.

* * * * *